(12) United States Patent
Olsen

(10) Patent No.: US 10,349,905 B2
(45) Date of Patent: Jul. 16, 2019

(54) DENTAL X-RAY SENSOR HOLDER

(71) Applicant: Steven C. Olsen, Centennial, CO (US)

(72) Inventor: Steven C. Olsen, Centennial, CO (US)

(*) Notice: Subject to any disclaimer, the term of this patent is extended or adjusted under 35 U.S.C. 154(b) by 204 days.

(21) Appl. No.: 15/497,070

(22) Filed: Apr. 25, 2017

(65) Prior Publication Data
US 2018/0303442 A1  Oct. 25, 2018

(51) Int. Cl.
*A61B 6/14* (2006.01)
*A61B 6/00* (2006.01)

(52) U.S. Cl.
CPC .............. *A61B 6/145* (2013.01); *A61B 6/425* (2013.01); *A61B 6/587* (2013.01)

(58) Field of Classification Search
CPC .......... A61B 6/145; A61B 6/425; A61B 6/587
USPC ............... 378/38–40, 62, 204, 208
See application file for complete search history.

(56) References Cited

U.S. PATENT DOCUMENTS

| 2004/0213382 A1* | 10/2004 | Andell | A61B 6/145 378/197 |
| 2011/0164733 A1* | 7/2011 | Steward, Jr. | G03B 42/04 378/170 |

* cited by examiner

*Primary Examiner* — Courtney D Thomas
(74) *Attorney, Agent, or Firm* — Edwin H. Crabtree; Ramon L. Dizarro

(57) ABSTRACT

A dental x-ray sensor holder adapted for engaging a portion of an x-ray tube and holding a digital sensor inside a patient's mouth. The holder includes a holder base arm with a first and second tube arm. The first and second tube arms are adapted for engaging a portion of a side of the x-ray tube and hold the tube in a fixed position next to a patient's cheek. The holder also includes a buccal arm adapted for receipt inside the patient's mouth and next to a buccal side of a tooth under review. The buccal arm includes an elongated arm opening for receiving a portion of a sliding interoral position arm. The position arm is attached to a digital x-ray sensor. The position arm is used to adjust the sensor in the middle of the patient's mouth.

17 Claims, 4 Drawing Sheets

DENTAL X-RAY SENSOR HOLDER

BACKGROUND OF THE INVENTION (a) Field of the Invention

This invention relates to an x-ray holder and more particularly, but not by way of limitation, to a dental x-ray sensor holder used for holding a digital sensor or film in a proper oriented position inside the middle of a patients mouth, when taking an x-ray of a tooth.

(b) Discussion of Prior Art

Heretofore, prior art x-ray sensor holders and film holders are quite often placed imprecisely next to an inside of a tooth being x-rayed. When a dental patient bites down on a bite wing, holding the sensor or film, the sensor or film engages a side of a roof of the patient's mouth next to a gum line, thus causing discomfort. Also, with prior art holders using a tube guide ring disposed around a portion of an x-ray tube, proper alignment between the tube and the sensor is imprecise, the x-ray is quite often flawed, and cone cutting can occur. Further, holders using the tube guide ring around the x-ray tube are awkward and cumbersome to use and uncomfortable in the patient's mouth.

The subject dental x-ray sensor holder eliminates the above mentioned problems related to discomfort to a dental patient and provides for proper alignment of an x-ray sensor in the middle of the patient's mouth.

SUMMARY OF THE INVENTION

In view of the foregoing, it is a primary objective of the subject invention to provide a dental x-ray sensor holder for holding a digital sensor or film in a proper position inside a patient's mouth, with proper alignment and orientation with an x-ray tube. This structural feature of the invention greatly improves x-ray analysis of a tooth under repair for a tooth filling, a crown or other dental procedure.

Also another object of the invention is the holder includes a buccal arm. The buccal arm is placed next to a buccal side of a tooth under review. This key feature provides for enhanced alignment between the x-ray tube, the sensor, with the tooth therebetween.

A key object of the holder is to provide for the proper placement of the digital sensor inside the middle of the mouth. This is done by having an elongated opening in the buccal arm for receiving one end of a sliding interoral position arm. An opposite end of the position arm is used to hold the sensor. The interoral position arm helps prevent the engagement of the top of the sensor against the roof of the patient's mouth, when biting down on the position arm.

The subject dental x-ray sensor holder includes a holder base arm with a first and second tube arm. The first and second tube arms are adapted for engaging a portion of a side of an x-ray tube to help hold the tube in a fixed position next to a patient's cheek. The holder also includes a buccal arm. The buccal arm is adapted for receipt inside the patient's mouth and next to a buccal side of a tooth under review. The buccal arm includes an elongated opening for receiving one end of a sliding interoral position arm. The interoral position arm is adapted to be engaged by the patient's teeth, when the x-ray is being taken. An opposite end of the position arm is attached to a digital sensor. The sensor is held in the middle of the patient's mouth and is used to receive the x-ray from the x-ray tube and through the tooth under review.

These and other objects of the present invention will become apparent to those familiar with the use of dental x-ray sensor holders when reviewing the following detailed description, showing novel construction, combination, and elements as herein described, and more particularly defined by the claims, it being understood that changes in the embodiments to the herein disclosed invention are meant to be included as coming within the scope of the claims, except insofar as they may be precluded by the prior art.

BRIEF DESCRIPTION OF THE DRAWINGS

The accompanying drawings illustrate complete preferred embodiments in the present invention according to the best modes presently devised for the practical application of the subject x-ray sensor holder, and in which.

DETAILED DESCRIPTION OF THE PREFERRED EMBODIMENTS

Figures 1, 2:
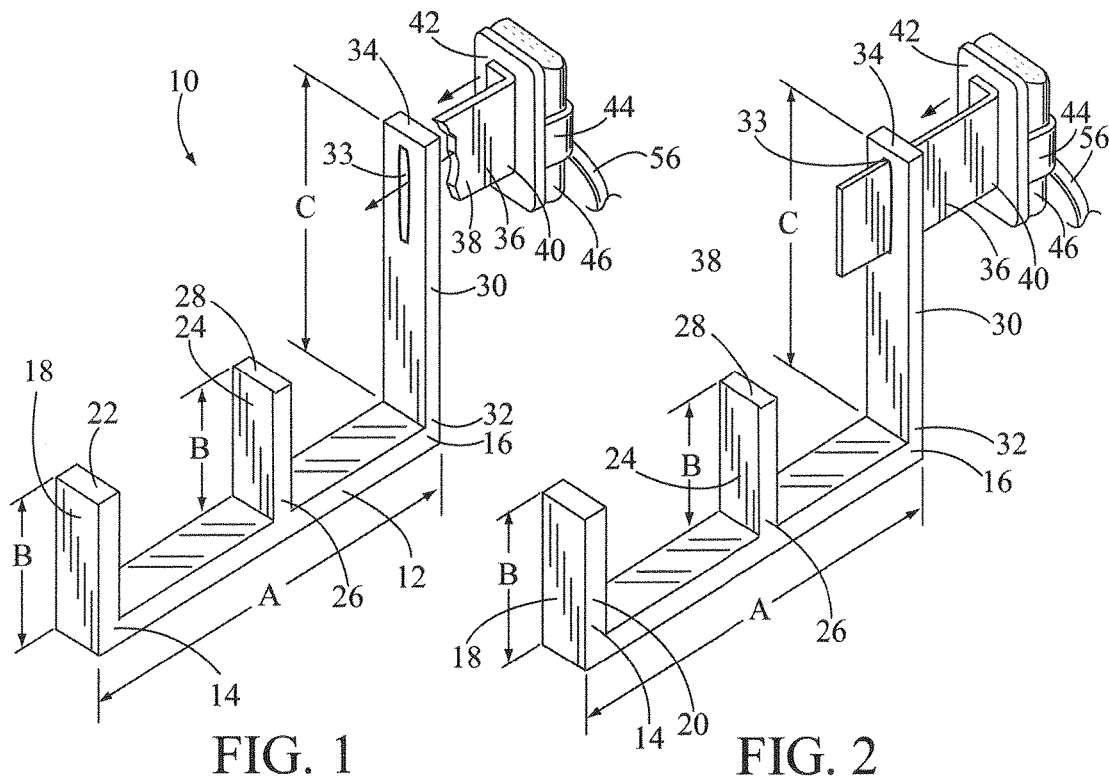
FIG. 1 is a perspective view of the dental x-ray sensor holder and illustrating a holder base arm, a first and second tube arm attached to the base arm, and a buccal arm attached to the base arm. The buccal arm includes an elongated arm opening for receiving one end of a sliding interoral position arm.
FIG. 2 is another perspective view of the sensor holder with a portion of the sliding interoral position arm received through the elongated opening in the buccal arm.

In FIG. 1, a perspective view of the dental x-ray sensor holder is shown having general reference numeral 10. The sensor holder 10 includes a holder base arm 12 having a first end 14 and a second end 16. The holder base arm 12 has a length "A", in a range of 6 to 8 inches.

The sensor holder 10 includes a first tube arm 18 having a first end 20 and a second end 22. The first end 20 is attached to the first end 14 of the base arm 12 and disposed at right angles thereto. The first tube arm 18 has a length "B", in a range of 2 to 3 inches.

Also, the sensor holder 10 includes a second tube arm 24 having a first end 26 and a second end 28. The first end 26 is attached to a portion of the base arm 12 and disposed at right angles thereto. The second tube arm 24 is parallel to and spaced apart from the first tube arm 18. Also, the second tube arm 24 has a length "B", in a range of 2 to 3 inches.

Figure 3:
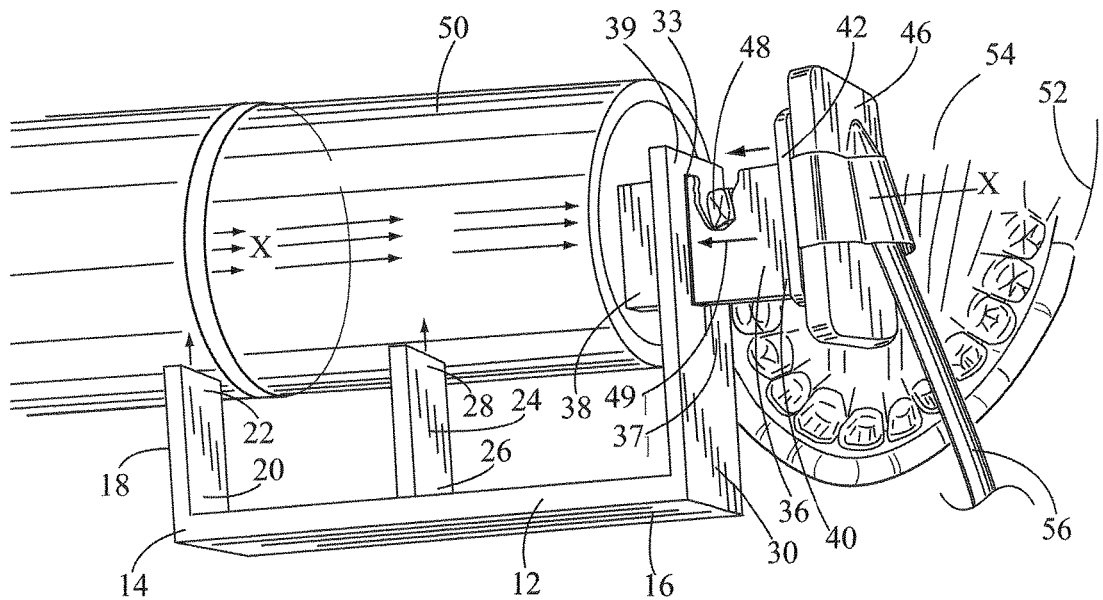
FIG. 3 is a top perspective view of the buccal arm placed next to a buccal side of a rear molar of a patient's lower teeth. The x-ray sensor is positioned in the center of the patient's mouth using the sliding interoral postion arm. A portion of an x-ray tube is shown placed next to a cheek of the dental patient.
Figure 4:
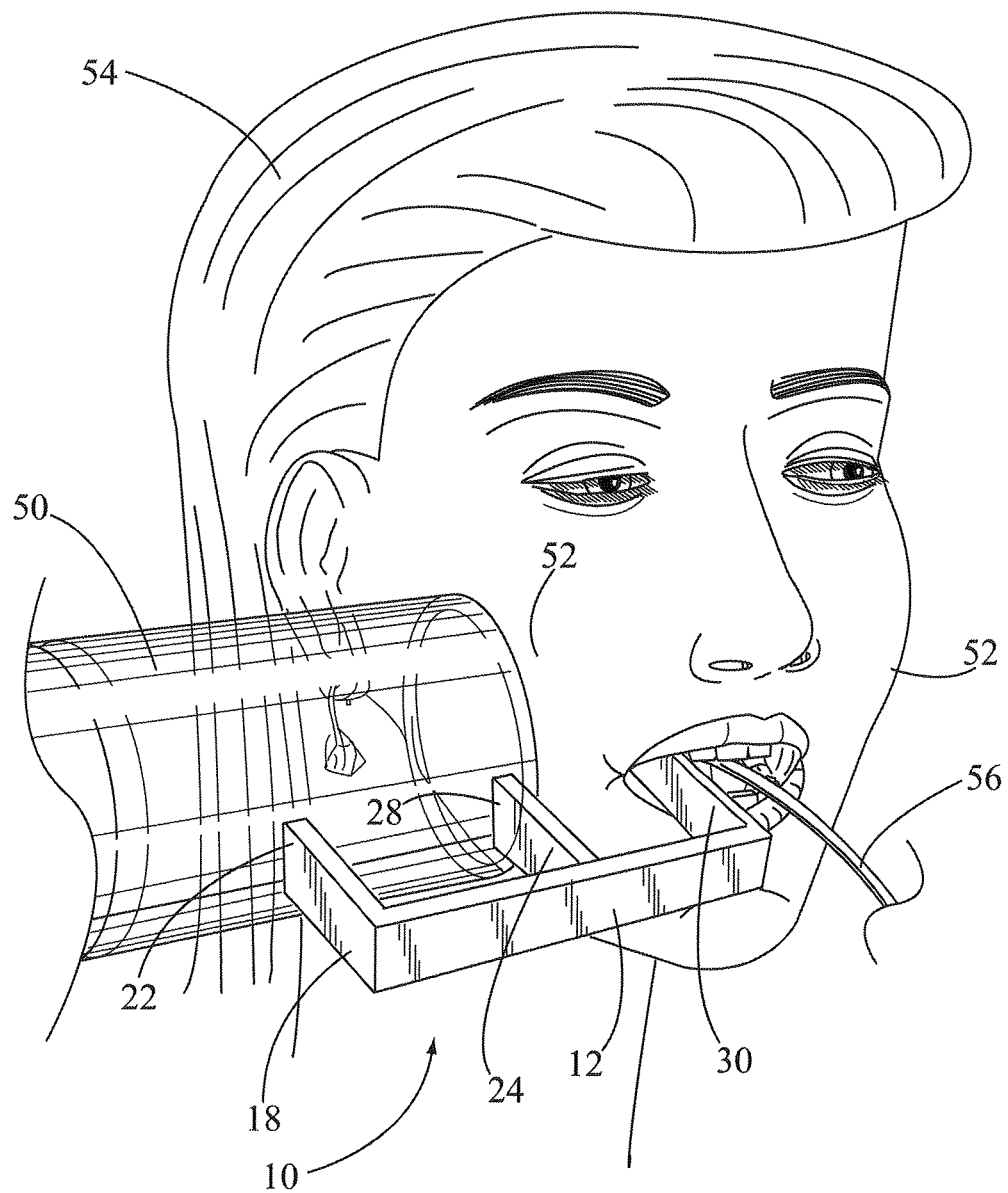
FIG. 4 is another perspective view of the sensor holder illustrating the dental patient with the buccal arm and the interoral position arm with attached digital sensor received inside the patient's mouth and oriented for an x-ray of the patient's tooth.

Further, the sensor holder 10 includes an elongated buccal arm 30 having a first end 32 and a second end 34. The first end 32 is attached to the second end 16 of the base arm 12 and at right angles thereto. The buccal arm 30 is adapted for receipt inside a patient's mouth, as shown in FIGS. 3 and 4. The buccal arm 28 has a length "C" in a range of 3 to 4 inches.

Still further, the buccal arm 30 includes an elongated arm opening 33 adapted for receiving a sliding interoral position arm 36. The position arm 36 includes one end 38 and an opposite end 40. The one end 38 is slidably received through the arm opening 33. The opposite end 40 of the position arm 36 is attached to a position arm base 42. The arm base 42 includes a sensor strap 44 for holding a digital sensor 46 thereon.

In FIG. 2, another perspective view of the sensor holder 10 is shown. In this view, the first end 38 of the sliding interoral position arm 36 is shown received through the elongated arm opening 33 for adjusting the digital x-ray sensor 46 in the middle of the patients mouth. The position arm 36 has a length, in a range of 2 to 5 inches, which is sufficient for proper adjustment of the sensor 46.

It should be noted when viewing the holder 10 in the above mentioned drawings, the various arms making up the holder have a width in a range of ½ to ¾ inches for ease in receipt in the patient's mouth. Also, the arms have an angular configuration.

In FIG. 3, a top perspective view of the buccal arm 30 is shown and placed inside a patient's mouth and next to a buccal side of a rear molar 48 of a patient's lower teeth. A portion of the interoral position arm 36 has been cutaway to illustrate the rear molar 48. Also, the end portion 38 of the position arm 36 is shown, as indicated by arrow 49, has been slide through the elongated arm opening 33 for the proper adjustment of the digital sensor 46 in the middle of the patient's mouth. The arm opening 33 is parallel to a length of the buccal arm 30 and centered thereon. In this drawing, a lower portion 37 of the buccal arm 30 is disposed next to the lower teeth. An upper portion 39 of the buccal arm 30 is disposed next to the upper teeth.

In FIG. 3, an end portion of an x-ray tube 50 is shown placed next to a cheek 52 of a dental patient 54. In this drawing, it is important to note the x-ray tube 50 is properly aligned with the sensor 46, using the buccal arm 30 next to the rear molar 48 under review, and oriented along lines X-X. Radiation arrows 55 are shown passing through the tube 50, through the buccal arm 30, through the molar 48 and to the digital sensor 46. The sensor 46 is shown connected to an electrical line 56, which leads to a x-ray machine. The x-ray machine is not shown in the drawings.

In FIG. 4, another perspective view of the dental patient 54 is shown with the buccal arm 30, the interoral position arm 36, and the attached digital sensor 46 received inside her mouth and properly oriented for an x-ray of the patient's tooth under review. It should be noted, the second ends 22 and 28 of the first and second tube arms 18 and 24 are held against a portion of a side of the x-ray tube 50. The two tube arms provide stability of the tube 50 pressed against the patient's cheek 52 and help in the orientation, along lines X-X, with the baccal arm 30 and the sensor 46.

Figure 5:
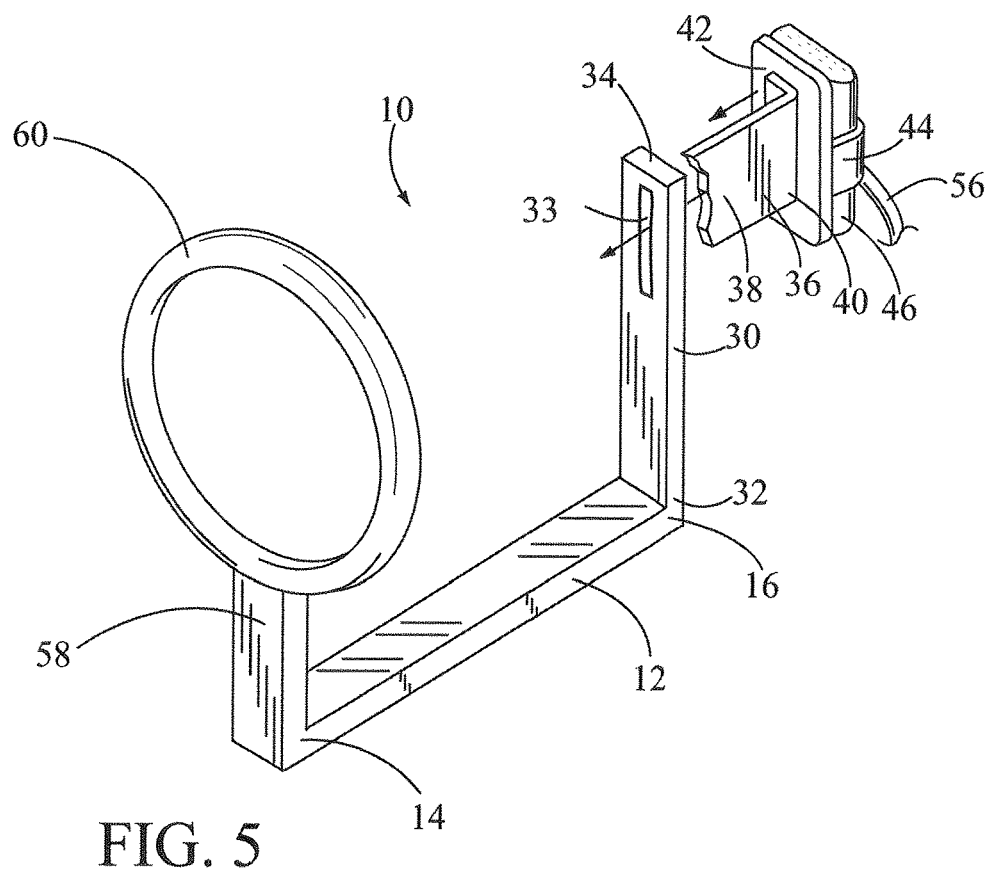
FIG. 5 is an alternate embodiment of the sensor holder and similar to FIG. 1. In this drawing, the holder base arm is shown having an upwardly extending ring arm. The ring arm is attached to tube ring, which is adapted for receipt around a portion of the x-ray tube.

In FIG. 5, an alternate embodiment of the x-ray sensor holder 10 is illustrated and similar to FIG. 1. In this drawing, the holder base arm 12 includes an upwardly extending ring arm 58. The ring arm 58 is attached to a tube ring 60. The tube ring 60 is adapted for receipt around a portion of the x-ray tube 50. Obviously, the ring arm 58 and the tube ring 60 are used for holding the x-ray sensor holder 10 in place and in lieu of the first and second tube arms 18 and 24.

Figure 6:
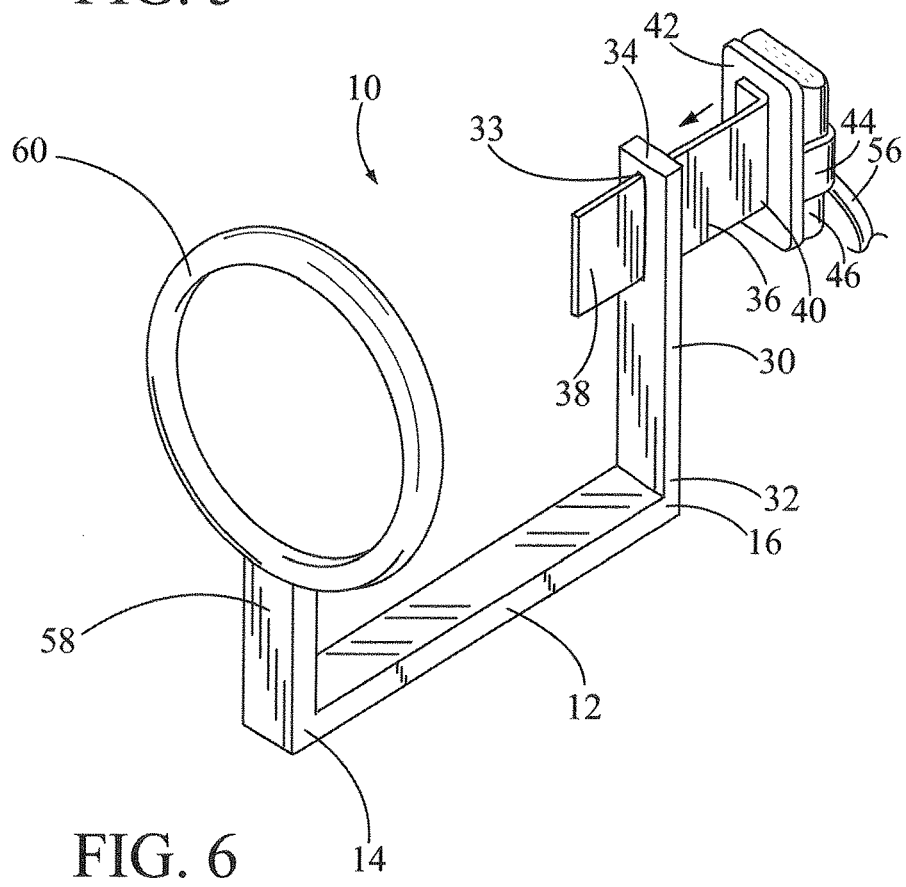
FIG. 6 is similar to FIG. 5 and illustrates the portion of the sliding interoral position arm received through the elongated opening in the buccal arm.

In FIG. 6, which is similar to FIG. 5, a portion of the sliding interoral position arm 36 is shown received through the elongated opening 33 in the buccal arm 30.

Figure 7:
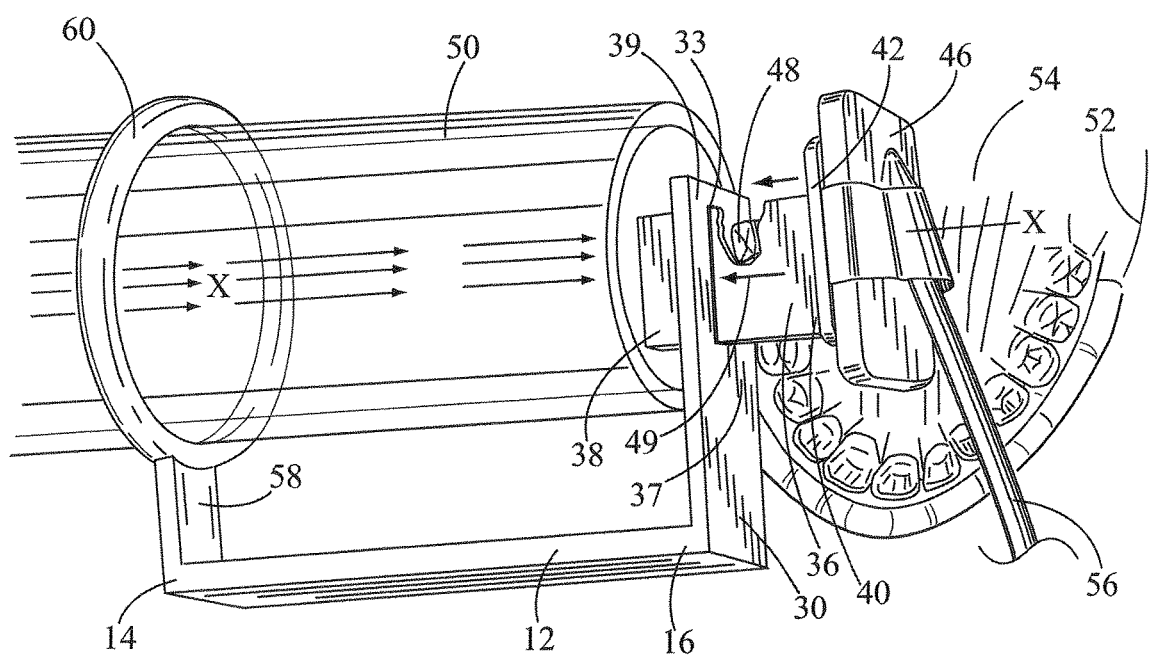
FIG. 7 is similar to FIG. 3 and illustrates the tube ring received around the x-ray tube for holding the buccal arm in place inside the patient's mouth and next to the outside of the molar under review.

In FIG. 7, which is similar to FIG. 3, the tube ring 60 is shown received around the x-ray tube 50. In this manner, the tube ring 60 holds the buccal arm 30 in place inside the patient's mouth and next to the outside of the molar 48 under review.

While the invention has been particularly shown, described and illustrated in detail with reference to the preferred embodiments and modifications thereof, it should be understood by those skilled in the art that equivalent changes in form and detail may be made therein without departing from the true spirit and scope of the invention as claimed except as precluded by the prior art.

The invention claimed is:

1. A dental x-ray sensor holder adapted for engaging a portion of an x-ray tube and adapted for holding a digital sensor inside a patient's mouth, the holder comprising:
   a holder base arm;
   a first tube arm and a spaced apart second tube arm, the first and second tube arms attached to the base arm and at right angles thereto, the first and second tube arms are adapted for engaging a side of the x-ray tube;
   a buccal arm attached to the base arm and at right angles thereto, the buccal arm adapted for receipt inside the patient's mouth and next to a buccal side of a tooth under review, the buccal arm including a lower portion adapted for and disposed next to the lower teeth of the patient's mouth, the buccal arm including an upper portion adapted for and disposed next to the upper teeth of the patient's mouth; and
   an elongated arm opening in the buccal arm, the arm opening adapted for receiving one end of a sliding interoral position arm, the position arm attached to the digital sensor.

2. The holder as described in claim 1 wherein the elongated arm opening is parallel to a length of the buccal arm and centered thereon.

3. The holder as described in claim 1 wherein the first tube arm is attached to a first end of the base arm and the buccal arm is attached to a second end of the base arm.

4. The holder as described in claim 1 wherein the first tube arm has a first end attached to the base arm and the second tube arm has a first end attached to the base arm, wherein the first tube arm has a second end adapted for engaging the side of the x-ray tube and the second tube arm has a second end adapted for engaging the side of the x-ray tube.

5. The holder as described in claim 1 wherein the base arm has a length "A" in a range of 6 to 8 inches.

6. The holder as described in claim 1 wherein the first and second tube arms have a length "B" in a range of 2 to 3 inches.

7. The holder as described in claim 1 wherein the buccal arm has a length "C" in a range of 3 to 4 inches.

8. A dental x-ray sensor holder adapted for engaging a portion of an x-ray tube and adapted for holding a digital sensor inside a patient's mouth, the holder comprising:
   a holder base arm;
   a first tube arm and a spaced apart second tube arm, the first and second tube arms attached to the base arm and at right angles thereto, the first tube arm attached to one end of the base arm, the first and second tube arms are adapted for engaging a side of the x-ray tube;

an angular-shaped buccal arm attached to an opposite end of the base arm and at right angles thereto, the buccal arm having a width in a range of ½ to ¾ inches, the buccal arm adapted for receipt inside the patient's mouth and next to a buccal side of a tooth under review, the buccal arm including a lower portion adapted for and disposed next to the lower teeth of the patient's mouth, the buccal arm including an upper portion adapted for and disposed next to the upper teeth of the patient's mouth; and an elongated arm opening in the buccal arm, the arm opening adapted for receiving one end of a sliding interoral position arm, the position arm attached to the digital sensor.

9. The holder as described in claim 8 wherein the elongated arm opening is parallel to a length of the buccal arm and centered thereon.

10. The holder as described in claim 8 wherein the first tube arm has a first end attached to the base arm and the second tube arm has a first end attached to the base arm, wherein the first tube arm has a second end adapted for engaging the side of the x-ray tube and the second tube arm has a second end adapted for engaging the side of the x-ray tube.

11. The holder as described in claim 8 wherein the base arm has a length "A" in a range of 6 to 8 inches.

12. The holder as described in claim 8 wherein the first and second tube arms have a length "B" in a range of 2 to 3 inches.

13. The holder as described in claim 8 wherein the buccal arm has a length "C" in a range of 3 to 4 inches.

14. A dental x-ray sensor holder adapted for engaging a portion of an x-ray tube and adapted for holding a digital sensor inside a patient's mouth, the holder comprising:

a holder base arm;

a ring arm, the ring arm attached to the base arm and at right angles thereto;

a tube ring, the tube ring mounted on top of the ring arm, the ring arm adapted for receipt around a portion of the x-ray tube:

a buccal arm attached to the base arm and at right angles thereto, the buccal arm adapted for receipt inside the patient's mouth and next to a buccal side of a tooth under review, the buccal arm including a lower portion adapted for and disposed next to the lower teeth of the patient's mouth, the buccal arm including an upper portion adapted for and touching the upper teeth of the patient's mouth for proper alignment in the patient's mouth; and an elongated arm opening in the buccal arm, the arm opening adapted for receiving an interoral position arm, one end of the position arm received through the elongated arm opening and adjusted thereon, an opposite end of the position arm adapted for attachment to the digital sensor.

15. The holder as described in claim 14 wherein the elongated arm opening is parallel to a length of the buccal arm and centered thereon.

16. The holder as described in claim 14 wherein the sliding interoral position arm has a length, in a range of 2 to 5 inches, which is sufficient for proper adjustment of the sensor in the middle of the patient's mouth.

17. The holder as described in claim 14 wherein an opposite end of the sliding interoral position arm includes a sensor base with sensor strap for securing the digital sensor on the position arm.

* * * * *